United States Patent [19]
Leiner

[11] Patent Number: 5,496,521
[45] Date of Patent: Mar. 5, 1996

[54] ANALYZING DEVICE INCLUDING AN ION-PERMEABLE CHANNEL CONNECTING A SAMPLE CHAMBER WITH A REACTION SPACE

[75] Inventor: Marco Leiner, Graz, Austria

[73] Assignee: AVL Medical Instruments AG, Schaffhausen, Switzerland

[21] Appl. No.: 792,671

[22] Filed: Nov. 15, 1991

[30] Foreign Application Priority Data

Feb. 15, 1991 [AT] Austria ........................ 324/91

[51] Int. Cl.⁶ ................... G01N 21/05; G01N 21/47
[52] U.S. Cl. .............. 422/82.05; 422/58; 422/81; 422/82.06; 422/82.09; 422/86; 436/113; 436/122; 436/129; 436/163
[58] Field of Search ............ 422/58, 81, 82.04, 422/82.05, 82.06, 82.09, 86; 436/113, 122, 129, 163

[56] References Cited

U.S. PATENT DOCUMENTS

| | | | |
|---|---|---|---|
| 3,756,923 | 9/1973 | Dahms | 204/153.17 |
| 3,869,354 | 3/1975 | Montalvo, Jr. | 204/153.14 |
| 4,003,707 | 1/1977 | Lübbers et al. | 422/83 X |
| 4,973,561 | 11/1990 | Hansen et al. | 422/81 X |
| 5,081,041 | 1/1992 | Yafuso et al. | 422/82.06 X |
| 5,114,676 | 5/1992 | Leiner et al. | 422/82.06 |

FOREIGN PATENT DOCUMENTS

| | | |
|---|---|---|
| 390517 | 5/1990 | Austria . |
| 0105870 | 7/1984 | European Pat. Off. . |
| 326421 | 8/1989 | European Pat. Off. . |
| 2508637 | 11/1979 | Germany . |

OTHER PUBLICATIONS

M. Okada et al. *Kogyo Kagaku Zasshi* 1969, 72, 1407–1409.
M. E. Meyerhoff et al. *Anal. Chim. Acta* 1983, 154, 17–31.
J. F. Coetzee et al. *Anal. Chem.* 1986, 58, 650–653.

*Primary Examiner*—Robert J. Warden
*Assistant Examiner*—Arlen Soderquist
*Attorney, Agent, or Firm*—Watson, Cole, Grindle & Watson

[57] ABSTRACT

In a device for determining the concentration of a reagent from a group consisting of gases with acid or alkaline reaction in aqueous environments, and volatile acids and bases in liquid or gaseous samples, a sample chamber is situated in a housing and a unit for pH measurement with a reaction space is separated from the sample chamber by an ion-impermeable, gas-permeable membrane. The feeding of the reaction space with buffer solution is facilitated by connecting the reaction space by means of an ion-permeable channel to a reservoir for a buffer solution located outside of the pH measuring unit.

5 Claims, 4 Drawing Sheets

ANALYZING DEVICE INCLUDING AN ION-PERMEABLE CHANNEL CONNECTING A SAMPLE CHAMBER WITH A REACTION SPACE

BACKGROUND OF THE INVENTION

This invention relates to a device for determining the concentration of a reagent from the group of gases with acid or alkaline reaction in aqueous environments, and of volatile acids and bases in liquid or gaseous samples, comprising a sample chamber situated in a housing and a unit for pH measurement with a reaction space separated from the sample chamber by means of an ion-impermeable, gas-permeable membrane.

DESCRIPTION OF THE PRIOR ART

It is known, for instance, that the measuring of $CO_2$ or its partial pressure $pCO_2$ in liquids or gases may be inferred from a pH measurement. For this purpose a reaction chamber is required which is separated from the sample by an ion-impermeable, gas-permeable membrane, and in which the pH value is determined as given by the respective $pCO_2$ value of the sample. For calculation of the pH value the following equation may be employed:

$$pH = pK + \log \frac{cHCO_3^-}{\alpha \, pCO_2}$$

where pK ... pK value of the carbonic acid with pK=–log $K_c$ ($K_c$=dissociation constant)

α ... degree of dissociation of $CO_2$ $cHCO_3$ ... concentration of $HCO_3$— ions Similarly, the pH value may be changed in the reaction chamber by of $SO_2$. pH changes will also occur if an electrically neutral volatile acid, such as acetic acid or base, such as ammonia, enters the reaction chamber through the gas-permeable membrane.

In such instances care must be taken that the pH value of the reaction chamber not be affected by the current pH of the sample to be determined, while a gas exchange between sample and reaction chamber must be made possible.

It is further known that pH measurements may be performed in several different ways, for example, with optical methods using pH-dependent fluorescent dyes, pH-dependent absorption dyes or pH-dependent polymers (e.g., polyaniline), or with potentiometric techniques using ion-selective glass electrodes via an electro-chemical measuring chain, or with ion-sensitive or ion-selective field effect transistors (ISFETs), the height of the pH-dependent potential jump influencing the drain source current. Other devices for pH measurement include pH-sensitive solid state systems (e.g., noble metal/noble metal oxide systems), redox systems (quinhydrone electrode) or the antimony electrode.

An apparatus of the above type is disclosed in Austrian Pat. No. 390 517. The $CO_2$ sensor described there consists of a transparent supporting layer, a pH-sensitive indicator layer, a transparent as well as an opaque hydrogel layer and a $CO_2$-permeable, ion-impermeable membrane placed on the sample side. The hydrogel layers are impregnated with a buffer solution. In this manner the $CO_2$ partial pressure may be determined via the change in pH of the hydrogel layer adjacent to the indicator layer.

The pH of the reaction chamber will depend on the $pCO_2$ of the sample, and on the temperature and concentration of the buffer solution in tile reaction chamber. For a given temperature and concentration of the buffer solution, the pH of the reaction chamber will only depend on the $pCO_2$ of the sample.

Since the gas-permeable, ion-impermeable membrane will also be permeable to water by means of isothermal distillation, the gas exchange between sample chamber and reaction chamber will be accompanied by an exchange of water, which will entail a change in the concentration of the buffer solution. This unfavorable effect is encountered whenever the buffer solution in the reaction chamber has a vapor pressure different from that of the storage medium or the sample in the sample chamber.

The exchange process will reach a state of equilibrium only after the osmotic pressure has reached the same level in both chambers. The rate of the exchange process depends on the type and thickness of the material used. In order to obtain an arrangement with long-term stability, and to prevent tile reaction chamber from drying out, the sample chamber must be filled with a storage medium prior to measurement, which should have the same osomotic pressure as the medium in the reaction chamber.

Similar problems arise with the arrangement described in German Pat. No. 25 08 637, where a flat indicator chamber is separated from the sample by a membrane which is selectively permeable to the blood constituents to be measured. The pH value is determined by optical means using a pH-dependent fluorescent indicator.

In tile variant described in EP-A 0 105 870 the reaction space is constituted by aqueous droplets or hygroscopic place-holder materials uniformly distributed in a gas-permeable polymer membrane. pH-measurement is performed with the use of a pH-dependent fluorescent indicator contained in the droplets or place-holder materials.

With miniaturized measuring devices of this kind, the technique of filling the reaction space with a buffer solution of defined salt composition, and maintaining constant the concentration of the buffer solution, has proved to be most complex, even though it is basically possible to introduce the buffer salts into the hydrogel layer providing the reaction space first, before the formation of the ion-impermeable layer, i.e., by immersing the foil in a buffer solution and drying it subsequently. After the element has been built into the device the water may be introduced into the reaction space by filling the sample chamber with an isoosmotic buffer solution and isothermal distillation. It has been found, however, that with this technique the reaction space fills with water comparatively slowly and that the reproductbility of such filling puts high demands on the manufacturing process.

SUMMARY OF THE INVENTION

It is an object of the invention to improve a device of the above type such that it will permit fast and reproducible filling of the reaction space with a buffer solution while maintaining constant the concentration of the buffer solution until the measuring process takes place, and between individual measurements.

In the invention this is obtained by connecting the reaction space by means of an ion-permeable channel to a reservoir for a buffer solution located outside of the pH measuring unit.

By establishing a connection between the reaction space and a reservoir containing the buffer solution, the reaction space can be filled quickly and easily and is furthermore protected against desiccation by this connection.

An enhanced variant of the invention provides that tile sample chamber be used as a reservoir for the buffer solution, and that the ion-permeable channel link the reaction space and the sample chamber while bypassing the ion-impermeable, gas-permeable membrane. The advantage of this variant is that the sample chamber may simultaneously be used as a reservoir for the buffer solution. The ion-permeable channel is configured in such a way as to prevent the sample protons from entering the reaction space during the relatively short measuring period, while permitting a ionic exchange between the sample chamber acting as a reservoir and the reaction space during storage and between measurements. Diffusion times may be extended by suitable configuration of the channel or by filling the ion-permeable channel with ion-permeable material.

If optical sensors are employed the reaction space should be formed by an indicator layer covered with the ion-impermeable, gas-permeable membrane, which layer is in contact with the ion-permeable channel.

In a particularly favorable variant of the invention a sensor comprising a supporting layer, the indicator layer and tile ion-impermeable, gas-permeable membane is cemented or pressed or fitted into a depression in the lower part of a two-part housing, a recess on the side of the depression forming the ion-permeable channel in lateral contact with the indicator layer. For manufacture of a large number of identical measuring devices it has proved an advantage to apply the indicator layer forming the reaction space and the gas-permeable, ion-impermeable layer over a large area of a polymer foil acting as a supporting layer, before punching out a number of identical elements from this foil and attaching them to the two-part housing by pressing, fitting or cementing them in place in a suitably shaped depression in the channel-shaped lower part of this housing.

According to a further variant of the invention the sample chamber is provided with separate sample feeding and draining lines, one of which has a branchoff for feeding a buffer solution into the sample chamber, the ion-permeable channel departing from the reaction space opening into this branchoff. This type of measuring device is particularly well suited for multiple measurings, as the sample cannot enter the reaction space.

Finally, the invention provides for the possibility that the indicator substance of the indicator layer be dissolved in the buffer solution.

BRIEF DESCRIPTION OF THE DRAWINGS

The invention will be further described with reference to the accompanying drawings.

DETAILED DESCRIPTION OF PREFERRED EMBODIMENTS

Figure 1:
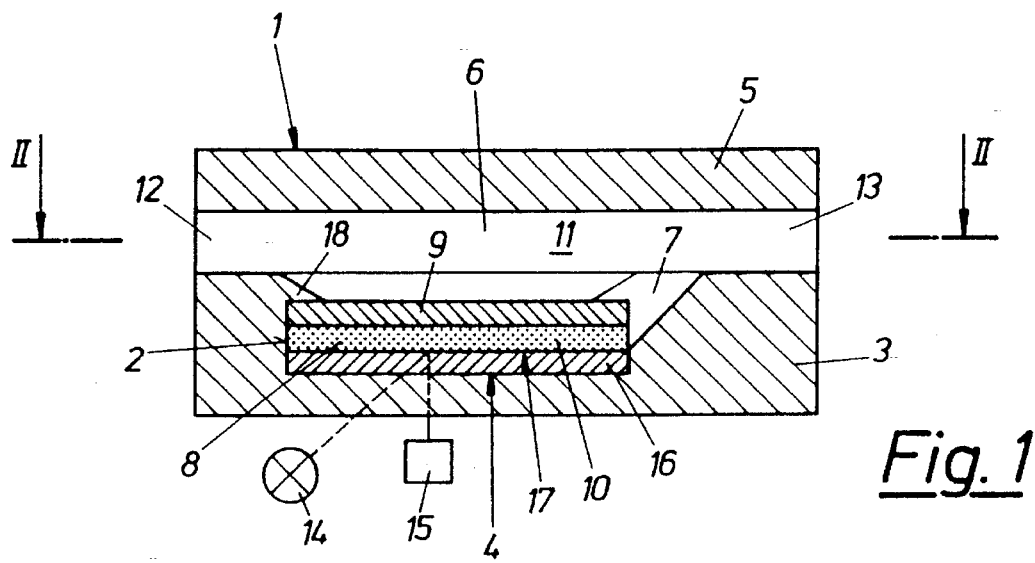
FIG. 1 is a section of a device of the invention along line I—I in FIG. 2.
Figure 2:
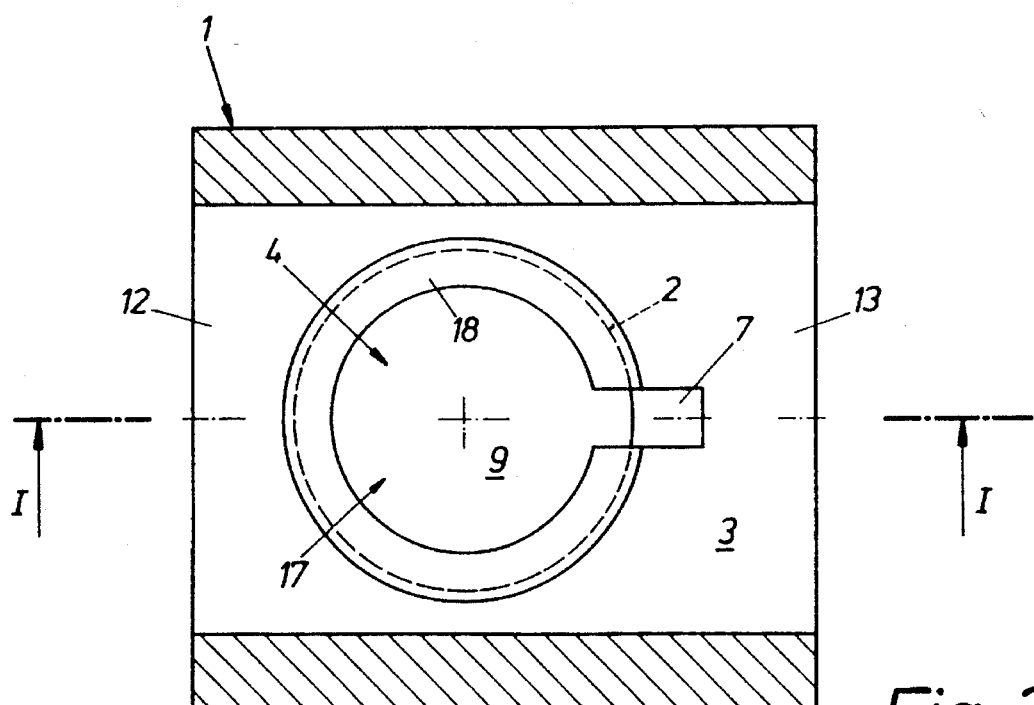
FIG. 2 is a section along line II—II in FIG. 1.

The device shown in FIGS. 1 and 2 for determining the concentration of a reagent, such as the $pCO_2$, in a liquid sample, has a two-part housing 1 containing the sensor 17 of a unit 4 for pH measurement in a depression 2 of its lower part 3. The upper part 5 of the housing 1 contains a sample chamber 6, which is connected to the reaction space 8 via an ion-permeable channel 7. In the variant shown here an indicator layer 10 covered by an ion-impermeable, gas-permeable membrane 9 is located in the reaction space 8, which layer 10 is laterally contacted by the ion-permeable channel 7. The sample chamber is simultaneously used as a reservoir 11 for the buffer solution, the ion-permeable channel 7 linking the reaction space 8 and the sample chamber 6 while bypassing the ion-impermeable membrane 9. From the sample feeder line 12 or the sample drainage line 13 the reaction space may be filled with buffer solution via channel 7, during which process the sample chamber is also fed with buffer solution, for which it serves as a reservoir 11 during storage of the measuring device or between two measuring cycles.

During the measuring process itself the sample enters the device through the sample feeder line 12, pushing the buffer solution out of the sample chamber 6. Any contact between the sample and the reaction space 8 or the indicator layer 10 is prevented during the short measuring period by configuring channel 7 as a capillary or by filling it with ion-permeable material, such that the diffusion time for ions is extended. Time periods during storage or between individual measuring cycles are long enough, however, to permit an exchange of ions between the reservoir 11 and the reaction space 8.

The measuring device consisting of light source 14 and detector 15 is indicated schematically only. It should be noted in this context that other devices for pH measurement as described in the opening paragraphs of this description are permissible, provided they have a suitable reaction space.

In the device presented in FIGS. 1 and 2, a supporting layer 16, the indicator layer 10 and the ion-impermeable, gas-permeable membrane 9 constitute the sensor 17, which is attached to the lower part 3 of the housing 1 by a pressed rim 18.

Apart from different methods of attaching the sensor 17 in the housing, the variants in FIGS. 3,4 and 5,6 correspond to those in FIGS. 1 and 2, respectively.

Figure 3:
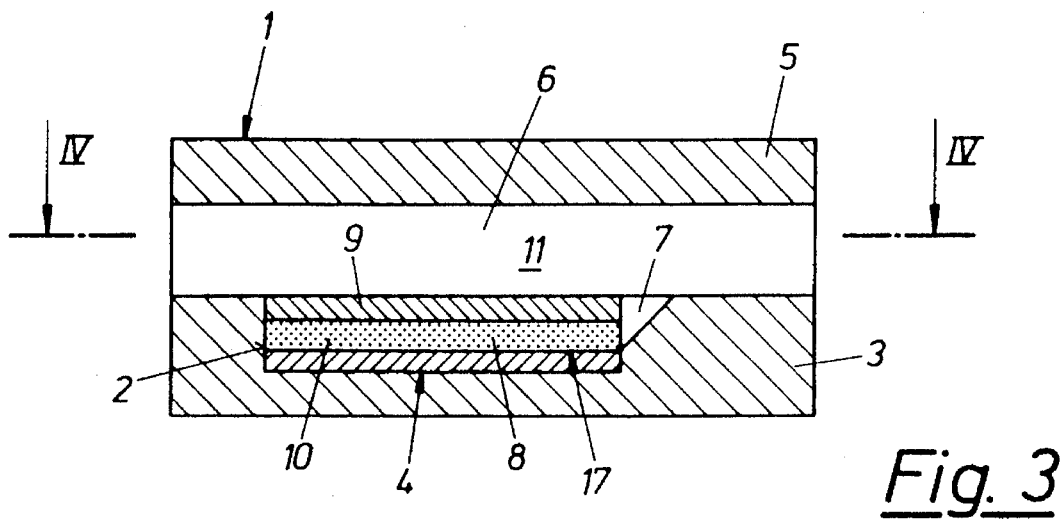
FIGS. 3 to 6 are variants of FIG. 1 in sections corresponding to FIG. 1 and 2, respectively.
Figure 4:
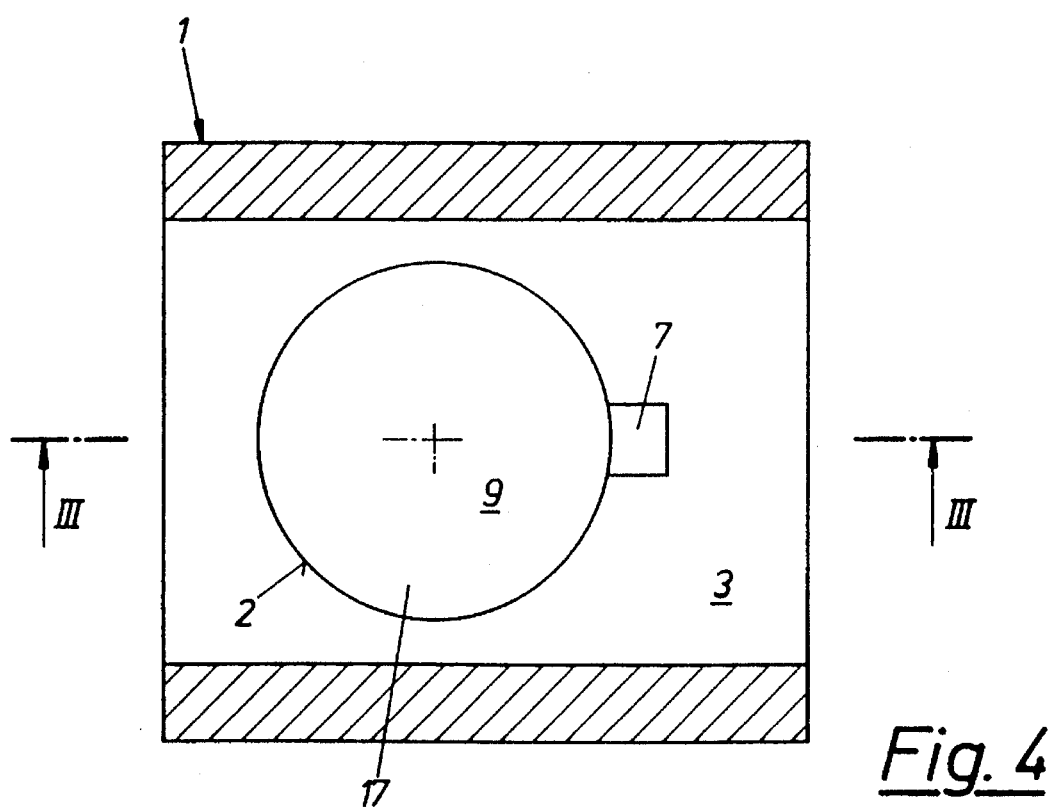

According to FIGS. 3 and 4, for instance, the sensor 17 may be cemented into the depression 2 of the lower part 3 so as to be completely flush with the bottom of the sample chamber, a recess on tile side of the depression 2 forming the ion-permeable channel 7.

Figure 5:
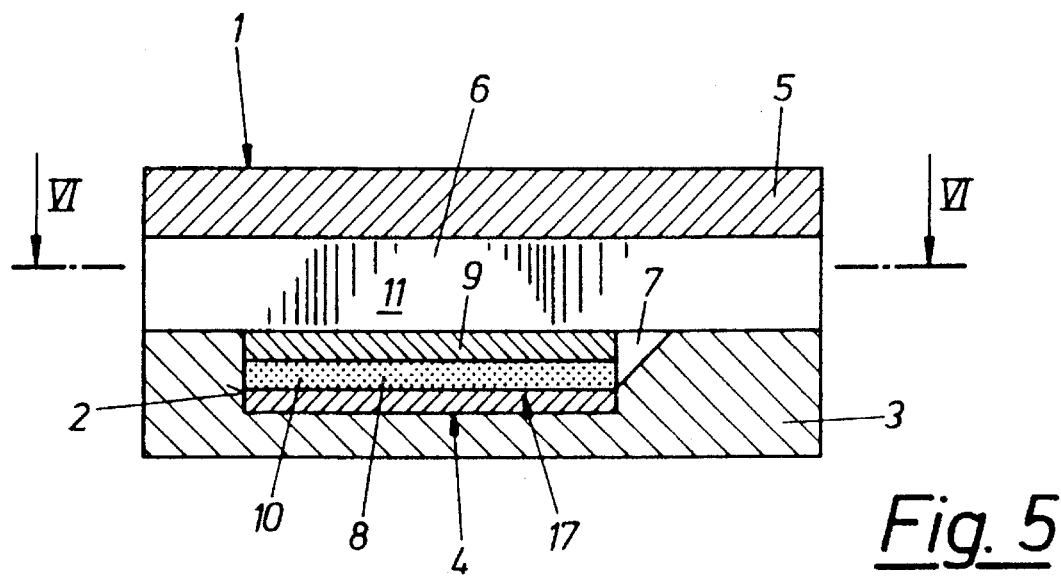
Figure 6:
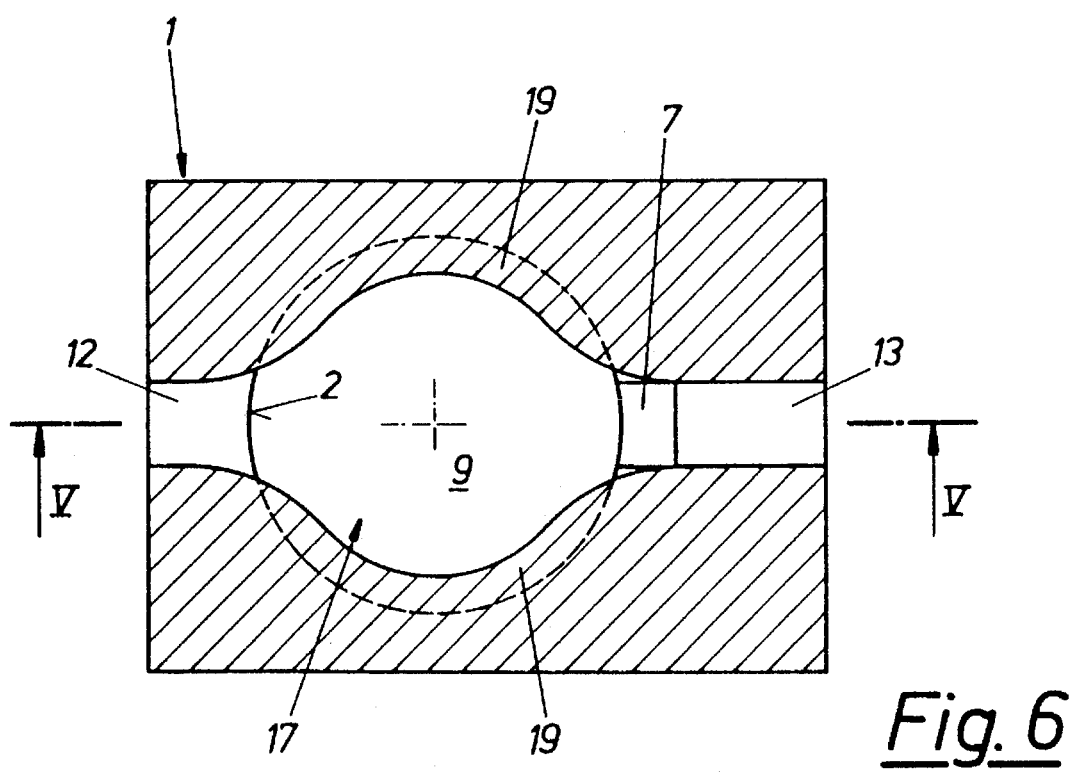

Another possibility, which is shown in FIGS. 5 and 6, would be to configure the sample chamber 6 in the upper part 5 of the housing 1 with a diameter smaller than that of the depression 2 or the sensor 17 located therein. When the lower part 3 and the upper part 5 are assembled to form the housing 1, the sensor 17 is held in place by the overlap 19 of the upper part 5.

Figure 7:
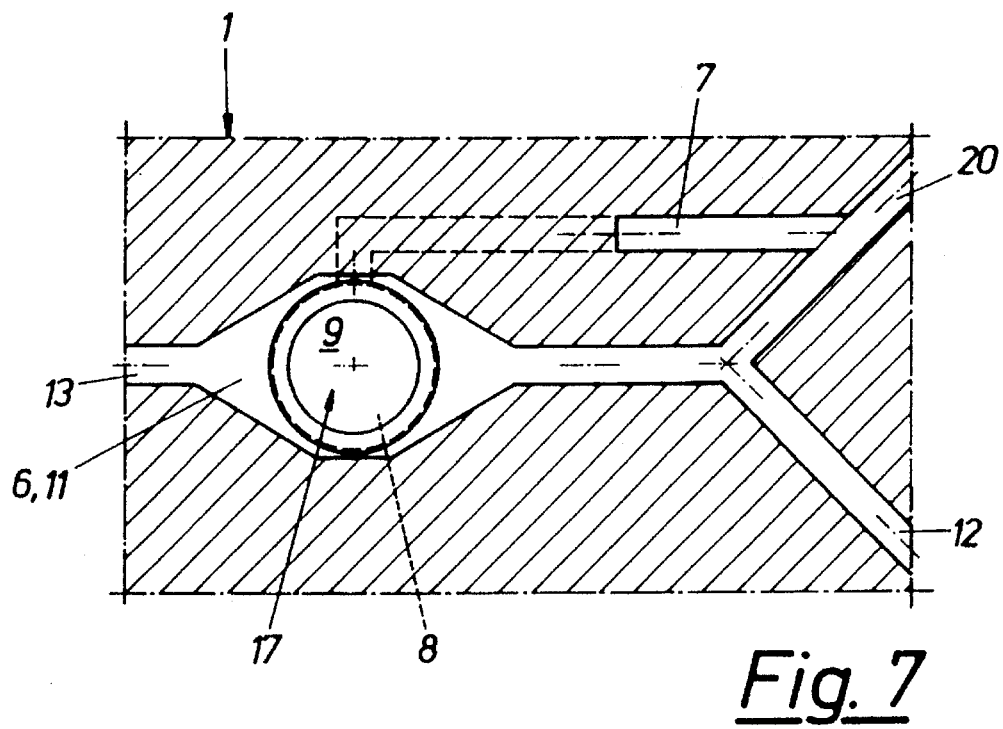
FIGS. 7 and 8 are further variants of the invention.

In the variant shown in FIG. 7 the sample feeder line 12 has a branchoff 20, through which the sample chamber 6 or the reservoir 11 may be provided with a buffer solution. Since the ion-permeable channel 7 opens into this branchoff 20, the buffer solution can also enter the reaction space 8. If tile sample is introduced via the sample feeder line 12, the buffer solution in the branchoff 20 and in the channel 7 will prevent the sample or sample components from entering the reaction space 8 during the relatively short period of measurement.

Figure 8:
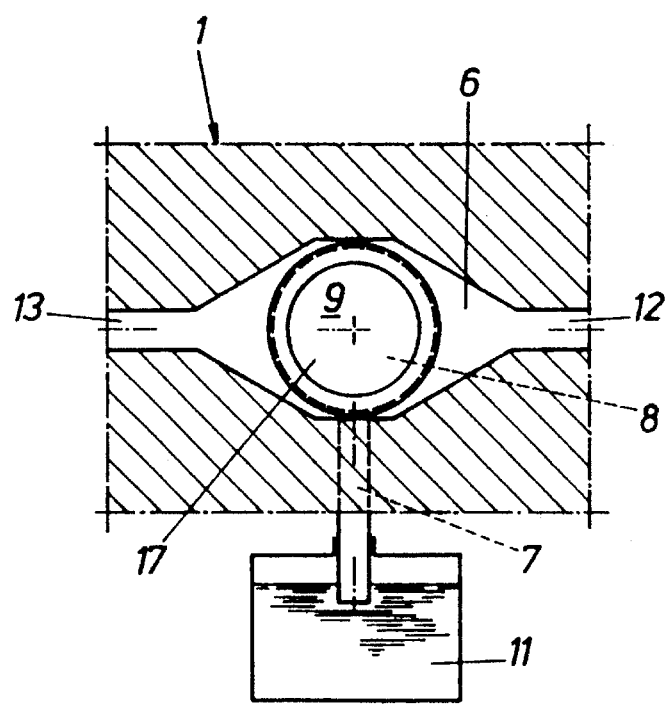

A simple variant is presented in FIG. 8. In this instance the reaction space 8 is connected to a separate reservoir 11 via the ion-permeable channel 7. Whereas in all other variants the buffer solution will simultaneously serve as a storage medium, a medium of the same osmolarity as the buffer solution but or different chemical composition may be used as a storage medium in this variant.

I claim:

1. A device for determining the concentration of a reagent from a group consisting of gases having an acid reaction in aqueous environments, gases having an alkaline reaction in aqueous environments, and volatile acids and bases in liquid or gaseous samples, comprising a housing defining a sample chamber, a unit for pH measurement with a reaction space separated from said sample chamber by an ion-impermeable, gas-permeable membrane, said sample chamber containing a buffer solution at least during storage, and means forming an ion-permeable channel configured as a capillary or filled with an ion-permeable material which connects said reaction space with said sample chamber while bypassing said ion-impermeable, gas-permeable membrane.

2. A device according to claim 1, wherein said reaction space contains an indicator layer covered by said ion-impermeable, gas-permeable membrane and wherein said indicator layer is in contact with said ion-permeable channel.

3. A device according to claim 2, comprising a two-part housing with a lower part having a depression, wherein a sensor comprising a supporting layer, said indicator layer and said ion-impermeable, gas-permeable membrane is cemented or pressed or fitted into said depression, and wherein said means forming said ion-permeable channel comprises a recess on one side of said depression such that said ion-permeable channel is in lateral contact with said indicator layer.

4. A device according to claim 2, including means forming separate sample feeding and drainage lines connected to said sample chamber, one of said feeding and drainage lines including a branchoff line for feeding a buffer solution into said sample chamber, and wherein said ion-permeable channel extends from said reaction space to said branchoff line.

5. A device according to claim 3, wherein an indicator substance of said indicator layer is dissolved in said buffer solution.

* * * * *